United States Patent [19]

Magaritz et al.

[11] Patent Number: 4,857,473
[45] Date of Patent: Aug. 15, 1989

[54] WATER SAMPLING SYSTEM

[75] Inventors: Mordeckai Magaritz, Rehovot; Daniel Ronen, Kfar Saba; Itzhak Levy, Ramat Gan, all of Israel

[73] Assignees: State of Israel, Ministry of Agriculture, Water Commission, Tel-Aviv; YEDA Research and Development Co., Ltd., Rehovot, both of Israel

[21] Appl. No.: 901,791

[22] Filed: Aug. 29, 1986

[30] Foreign Application Priority Data

Sep. 2, 1985 [IL] Israel ......................................... 76275

[51] Int. Cl.$^4$ .......................... G01N 1/16; G01N 1/20
[52] U.S. Cl. ....................................... 436/177; 436/28; 436/39; 436/178; 436/809; 422/68; 422/101; 73/61 R; 73/61.1 R; 73/863.23; 210/321.84; 210/500.21
[58] Field of Search ..................... 422/68, 101; 436/28, 436/39, 150, 177, 178, 808, 809, 810; 73/61 R, 61.1 R, 863.23; 210/321.65, 321.84, 500.21

[56] References Cited

U.S. PATENT DOCUMENTS

| | | | |
|---|---|---|---|
| 3,825,410 | 7/1974 | Bagshawe | 422/68 X |
| 4,092,117 | 5/1978 | Byrne | 422/68 X |
| 4,550,011 | 10/1985 | McCollum | 422/68 |

FOREIGN PATENT DOCUMENTS 0638861 12/1978 U.S.S.R. ........................... 73/863.23
0779851 11/1980 U.S.S.R. .

Primary Examiner—Michael S. Marcus
Assistant Examiner—Lynn M. Kummert
Attorney, Agent, or Firm—Browdy and Neimark

[57] ABSTRACT

The invention relates to a device for the sampling of liquids which permeate dialysis membranes, comprising cells bounded by two such membranes. The device according to the invention is suited for determining hydrochemical profiles of groundwater, in lakes and the like. The device according to the invention is a modular one, comprising a plurality of consecutive dialysis cells, spaced at predetermined intervals, in a support system. The sampler is introduced into the liquid and left there for an adequate period of time to establish an equilibrium. After removal, each of the cells is analysed and provides information on the composition of the liquid at the given depth.

10 Claims, 4 Drawing Sheets

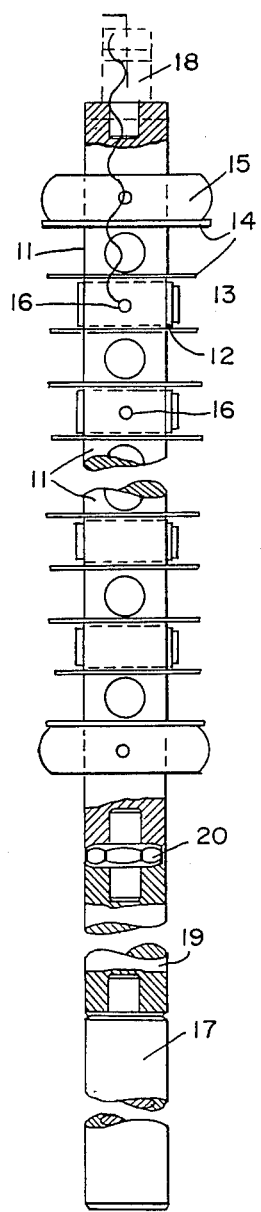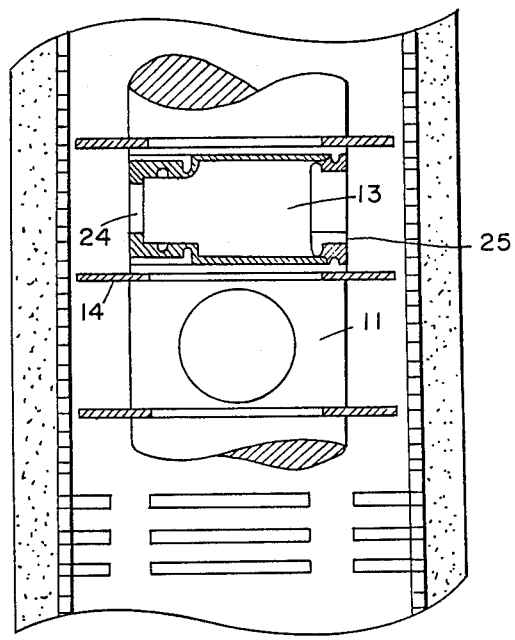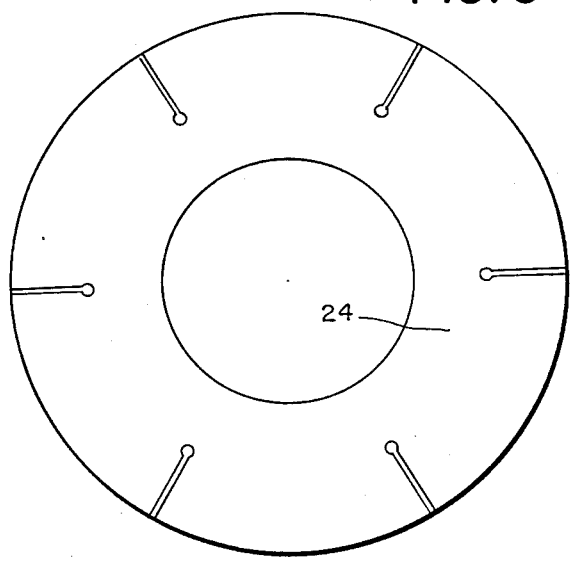
FIG. 1
FIG. 2
FIG. 3

FIG. 5
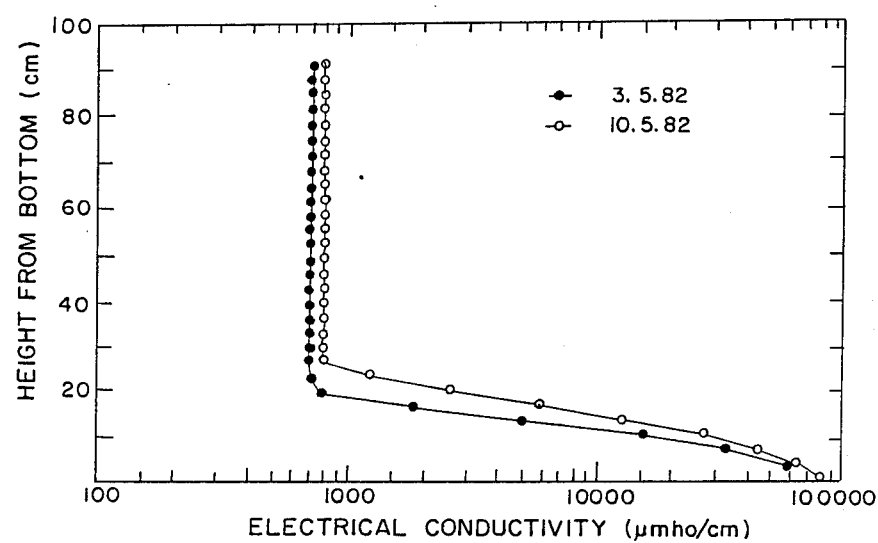
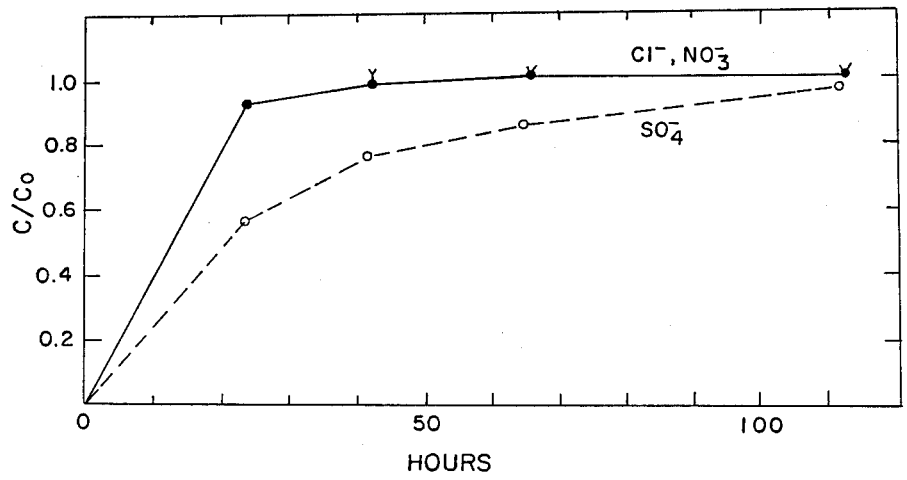
FIG. 6

WATER SAMPLING SYSTEM

FIELD OF THE INVENTION

According to the invention there is provided a modular water sampler for the sampling of hydrochemical profiles of groundwater, of water in lakes, ponds, reservoirs and the like. The sampler comprises a plurality of cells arranged at predetermined distances, each of which comprises dialysis membranes. The sampler is of special use in determining water quality profiles.

BACKGROUND OF THE INVENTION

The increasing needs of understanding the processes of groundwater contamination have necessitated the development of new, sampling techniques. In hydrochemical studies it is important to obtain small-interval-profiles of the examined water layer. Generally water samples are collected from pumping wells or by samplers lowered to different depths in research wells. These procedures disturb chemical gradients and yield only mixed water samples from different levels of the aquifer. In literature there have been described samples which have been used primarily for shallow aquifers. In most of these devices the water sample is pumped from the surface and the sampling intervals are of the order of 0.5 m.

Samplers developed for water studies in lakes employ the dialysis membrane technique which consists of placing a sampler having dialysis cells filled with distilled water at the sampling site and leaving it there for equilibration between the ambient water and the cell water. Sampling intervals of 1 cm have been achieved using this method.

The equilibration time of a dialysis cell system can be calculated using Fick's second law of diffusion.

SUMMARY OF THE INVENTION

The invention relates to a novel water sampling device which provides information about the chemical profile of a water layer at a certain depth, be it in a bore-hole, water-well or in a lake or the like.

The device is a modular sampler which can be assembled with a desired number of sampling cells, each of which provides information on a certain depth level. These can be arranged one after the other, and the diameter of these determines the sampling intervals. Generally sampling intervals of about 3 to 5 cm are satisfactory.

Each of the cells of the sampler comprises a tubular member closed at both its ends with a dialysis membrane. When such cells are arranged in a rod-like structure, the openings facing to the sides of the structure, the sampler can be introduced into a well, while they are filled with distilled water. The sampler is left in the well in a tranquil position for an adequate period of time to attain equilibrium with the surroundings, and when the sampler is removed, the water content of each cell can be analyzed, providing a profile for the layer defined by the cumulative length of the plurality of cells.

The sampler comprises a rod or pipe with a plurality of perpendicular throughgoing holes, each of which is adapted to accommodate a dialysis cell. A sampler was constructed with a plurality of cells of 3 cm diameter, but this value is not critical, and any other suitable diameter can be used. The cells are spaced from each other by a suitable seal made of a resilient material, of a diameter corresponding to that of the sampling well. Disk-shaped structures are mounted at both ends of the sampler to guide the structure through the well. Advantageously a weight is attached to the lower end of the sampler, and a hook for a suitable rope at its upper end. The sampler is constructed from modular elements, with each section comprising a predetermined number of dialysis cells, and with the possibility to assemble a sequence of such sub-units to result in the desired number of cells per sampler. It is also possible to construct the sampler from a plurality of such cells, one after the other.

A sampler of the invention is illustrated by way of example only with reference to the following description and drawings, which are of a schematical nature and not according to scale, and in which:

FIG. 1 is a side view of a sampler, in partial section;

FIG. 2 is an enlarged cross-sectional view through a part of the length of the sampler;

FIG. 3 is a plane view of a rubber seal of the sampler;

FIG. 5 illustrates the results of an equilibrium test;

FIG. 6 illustrates an electrical conductivity profile measured by a sampler of the invention;

DETAILED DESCRIPTION

Figure 4:
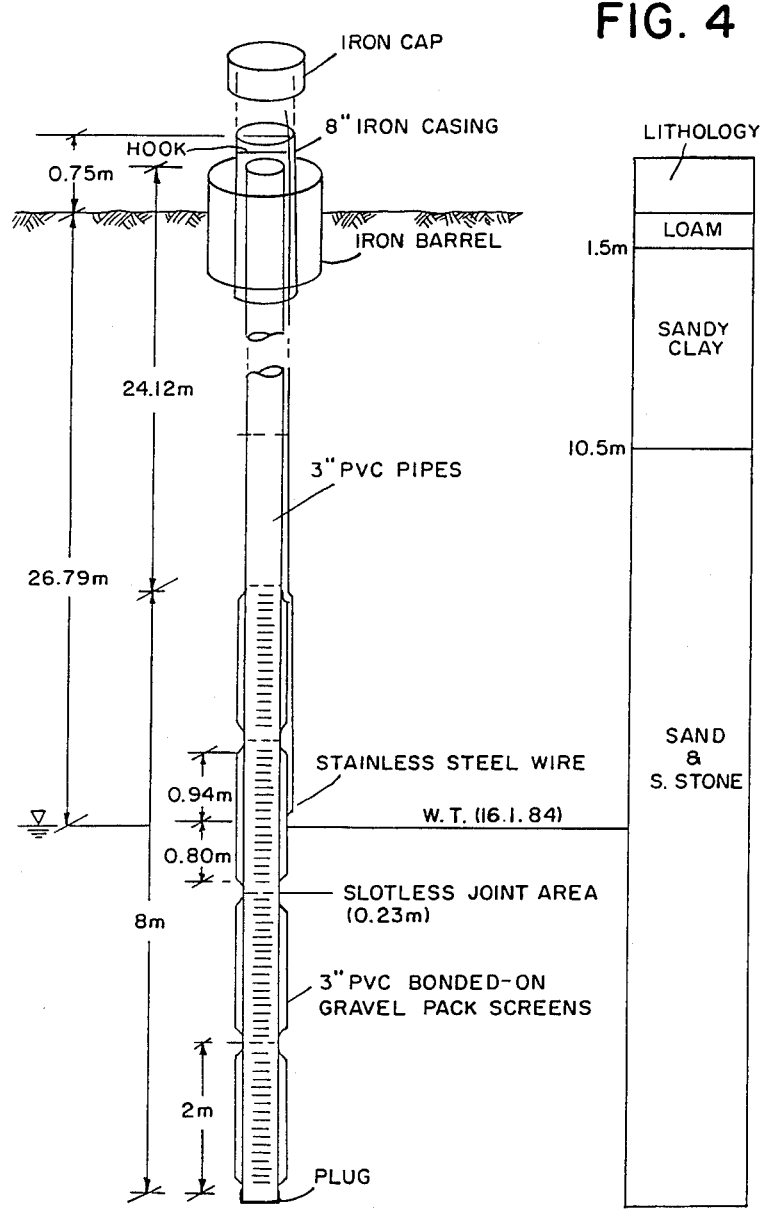
FIG. 4 is a schematic view of a research well and lithological profile.

As illustrated in FIGS. 1, 2 and 3, the device of the invention comprises a rod, made of a suitable plastic material, 11, of about 5 cm diameter, which has a length of about 135 cm, with 38 perpendicular criss-crossed holes 12, each of which accommodates a dialysis cell 13. These are spaced at 3 cm intervals and separated by flexible rubber seas 14. At the ends of the sampler there are provided two PVC rings 15, which serve to guide the sampler through the well. Such rings 15 can also be provided at predetermined intervals. The dialysis cells are secured in place by nylon screws 16. A coated weight 17 is connected to the lower end of the sampler. A nylon rope is attached to the upper holding segment 18. The sampler comprises advantageously a number of modular rod-segments 19, which can be connected by the double screw 20. The individual dialysis cells 13 are made of modified polyethylene vials 21, open at both ends, which are provided with closure rings 22 and 23, respectively, and with dialysis membranes 24 and 25, which can thus be easily replaced, and which are thus securely held in place.

The cells are filled with distilled water, or any other solutions closed by the membranes at both ends, and the sampler is introduced into the water (well, lake or the like) which is to be sampled and left to equilibrate with the surroundings. The sampler can thus be used with any water profile, be it a natural one or not. It can be used to determine the mineral content of ground water, for quality control in industrial processes, to determine contamination by oil spills, etc.

It is also possible to introduce electrodes into certain cells, and thus monitor from the surface the conductivity of the water in the cell, which is indicative of the ion content in the cell.

In order to determine empirically the equilibration time of the novel sampling system a laboratory test was performed where six pairs of dialysis cells were submerged in separated baths of a 800 ml ($Cl^- = 200$ mg $1^{-1}$; $NO_3^- = 100$ mg $1^{-1}$) that were mixed once each sampling day. (FIG. 5)

The performance of the sampler was tested measuring an Electrical Conductivity profile. The salinity gradient was artificially established by introducing a cold saline solution (1 gr cm$^{-3}$NaCl) at the bottom of a container filled with tap water. Two consecutive profiles were sampled after an equilibration period of 7 days. (FIG. 6)

The sampler is advantageously used in a screened well. As one of the aims of the system is to monitor the arrival of pollutants to the water table zone, we designed and drilled a research well for this special purpose which is described in FIG. 4. The well is located in the deep, sandy and phreatic Coastal Plain aquifer of Israel. The depth to the water table is 27 m and the thickness of the saturated 15 region about 130 m. The well was drilled by a spiral-driller dry method, without addition of water. PVC pipes were utilized. Bonded-on gravel pack screens were placed both above, 3 m, and below, 5 m, the water table (Pumpen-Boese-KK Filter 80/0.6/0.7-1.2, D. Klotz, 1979). The position of the screens in relation to the water table was selected to enable long-term sampling considering the both short and long term fluctuations (monthly to yearly) of the water table. A stainless steel wire mounted on one of the screens was connected to the surface by a PVC coated stainless steel wire.

The dialysis cells filled with distilled water were inserted into the sampler. The sampler, composed of two connected segments of MLFS, (multi-layer-floating sampler) with a total sampling length of 241 cm, was lowered into the research well. It was kept in position by attaching the nylon rope to the well hook. The exact position of the water table in relation to the dialysis cells was determined by connecting both stainless steel insulated wires to an ohmmeter. The sampler was left for an equilibration period of 30 days.

The 30 days sampling period was established to allow the re-equilibration of the well-aquifer system to "normal" hydrochemical conditions after lowering the sampler into the well (flow velocities in the aquifer range from 0.5 to 0.01 m.day$^{-1}$).

The MLFS is inexpensive and easy to operate. It may be lowered into any existing screened well and its sampling depth is not limited. Its dimensions are a function of the well diameter. The sampling volume is mainly defined in the desired sampling intervals.

The test system (sampler and research well), was specially built of PVC to permit also the future study of heavy metals in the water table zone.

The MLFS described was found suitable to obtain undisturbed groundwater samples at small vertical intervals enabling the measurement of chemical profiles in screened wells at any depth. The sampler can also be used for monitoring bodies of contaminated groundwater.

The device can be used for sampling and measuring the actual contaminant fluxes reaching the water table from the unsaturated zone before they are diluted in the main groundwater body.

A floating version of the sampler has further advantageous properties: Buoyancy permits the sampler to fluctuate inside the well according to the monthly variations of the water table. The single well dilution method can be applied to study the vertical profile of horizontal velocities in conjunction with the variation of chemical profiles.

Figure 7:
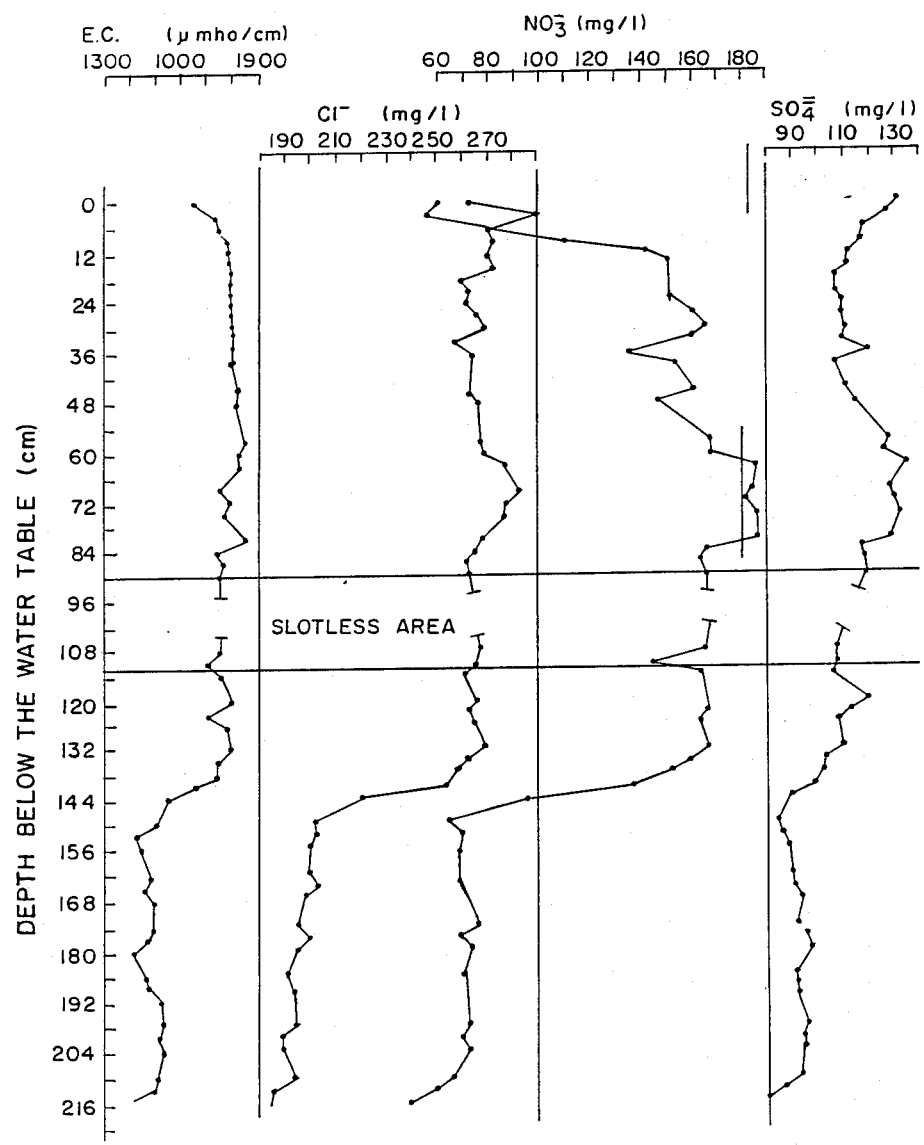
FIG. 7 illustrates the field profile measured in the research well of FIG. 4.

In the enclosed drawings, FIGS. 5 to 7 the following are presented:

FIG. 5 Equilibration test of dialysis cells conducted at 22° C. $-Cl^-$, $x-NO_3^-$, $o-SO_4^=$; each point represents two equilibration tests.

FIG. 6 Electrical conductivity profiles measured in a water tank by MLFS.

FIG. 7 Field profile of E.C., $Cl^-$, $NO_3^-$ and $SO_4^=$ as measured by MLFS in research well WT-2 (20.9.84).

We claim:

1. A method for establishing the chemical profile of the contaminants or constituents of a body of liquid comprising:

introducing into the body of liquid a sampling device in a substantially vertical orientation;

said sampling device comprising an elongated member having a longitudinal axis and having means defining a plurality of throughgoing holes at predetermined intervals, each of said plurality of holes having a longitudinal axis perpendicular to a longitudinal axis of said elongated member; and a plurality of dialysis cells, each of said plurality of cells being disposed in one of said plurality of throughgoing holes of said elongated member and each of said plurality of cells having first and second ends and a shape corresponding to a respective one of said plurality of throughgoing holes in which each of said plurality of cells is disposed so as to fit therewith, and each of said plurality of cells having dialysis membranes covering the first and second ends thereof;

leaving said sampling device in place, undisturbed, in the body of liquid until equilibrium is established within each of the dialysis cells of said sampling device; and removing the sampling device form the body of liquid; and analyzing the contents of each of said dialysis cells.

2. A method for establishing the chemical profile of the contaminants of constituents of the ground water in a screened well comprising:

introducing into a screen of the well a sampling device, said sampling device comprising an elongated member having a longitudinal axis and having means defining a plurality of throughgoing holes at predetermined intervals, each of said plurality of holes having a longitudinal axis perpendicular to a longitudinal axis of said elongated member; and a plurality of analysis cells, each of said plurality of cells being disposed in one of said plurality of throughgoing holes of said elongated member and each of said plurality of cells having first and second ends and a shape corresponding to a respective one of said plurality of throughgoing holes in which each of said plurality of cells is disposed so as to fit therewith, and each of said plurality of cells having dialysis membranes covering the first and second ends thereof;

a plurality of disk-shaped seals extending in a plane perpendicular to the longitudinal axis of said elongated member, one of said plurality of seals being disposed between each of said plurality of cells, each of said plurality of seals having a diameter slightly less than that of the screen into which the sampling device is to be inserted so as to seal each of said plurality of cells from the other cells of the device;

leaving said sampling device in place, undisturbed, in the well until equilibrium is established within each of the dialysis cells of said sampling device;

removing the sampling device form the well; and analyzing the content of each of said dialysis cells.

3. A sampling device for establishing the concentration and concentration profile of contaminants or constituents of a liquid to be sampled which are able to permeate through a dialysis membrane, comprising:

an elongated member having a longitudinal axis and having means defining a plurality of throughgoing holes at predetermined intervals, each of said plurality of holes having a longitudinal axis perpendicular to the longitudinal axis of said elongated member; and a plurality of dialysis cells, each of said plurality of cells being disposed in one of said plurality of throughgoing holes of said elongated member and each of said plurality of cells having first and second ends and a shape corresponding to a respective one of said plurality of throughgoing holes in which each of said plurality of cells is disposed so as to fit therewithin, and each of said plurality of cells having dialysis membranes covering the first and second ends thereof.

4. A sampling device in accordance with claim 3 for insertion into a screen of a well and further including a plurality of flexible disk-shaped seals extending in a plane perpendicular to the longitudinal axis of said elongated member, one of said plurality of seals being disposed between each of said plurality of cells, each of said plurality of seals having a diameter slightly less than that of the screen into which the sampling device is to be inserted so as to seal each of said plurality of cells from the other cells of the device when inserted into a screened well.

5. A sampling device in accordance with claim 4, wherein said elongated member further includes guide ring means for guiding the device when inserted into a screened well.

6. A sampling device in accordance with claim 3, comprising a plurality of said elongated members, each of said said elongated members having a plurality of closely spaced consecutive dialysis cells therewithin and being constructed and arranged to be longitudinally connected to one another.

7. A sampling device in accordance with claim 6, wherein each of said plurality of elongated members house from about 3 to about 50 individual consecutive dialysis cells arranged at intervals of about 3 to 10 cm.

8. A sampling device in accordance with claim 3, wherein each of said plurality of dialysis cells includes closure means for holding each of said dialysis membranes in place in a removable and replaceable manner.

9. A sampling device in accordance with claim 3, wherein said elongated member has an upper end and a lower end and further includes a weight at the lower end and attachment means for a rope at the upper end thereof.

10. A sampling device in accordance with claim 3, wherein at least one of said plurality of dialysis cells is provided with electrode means for making conductivity measurements within at least one cell and transmitting the results to a surface of the liquid being sampled when in use.

* * * * *